(12) United States Patent
Xiao

(10) Patent No.: US 11,630,821 B2
(45) Date of Patent: Apr. 18, 2023

(54) BLOCKCHAIN-BASED DATA PROCESSING METHOD AND APPARATUS, DEVICE, AND MEDIUM

(71) Applicant: Baidu Online Network Technology (Beijing) Co., Ltd., Beijing (CN)

(72) Inventor: Wei Xiao, Beijing (CN)

(73) Assignee: Baidu Online Network Technology (Beijing) Co., Ltd., Beijing (CN)

( * ) Notice: Subject to any disclaimer, the term of this patent is extended or adjusted under 35 U.S.C. 154(b) by 0 days.

(21) Appl. No.: 17/178,874

(22) Filed: Feb. 18, 2021

(65) Prior Publication Data

US 2021/0256015 A1 Aug. 19, 2021

(30) Foreign Application Priority Data

Feb. 19, 2020 (CN) .......................... 202010102672.9

(51) Int. Cl.
*G06F 16/23* (2019.01)
(52) U.S. Cl.
CPC ...... *G06F 16/2379* (2019.01); *G06F 16/2365* (2019.01)
(58) Field of Classification Search
None
See application file for complete search history.

(56) References Cited

U.S. PATENT DOCUMENTS

| 2019/0260574 A1 | 8/2019 | Shi et al. |
| 2019/0347653 A1 | 11/2019 | Lu et al. |
| 2020/0043007 A1 | 2/2020 | Simons |

(Continued)

FOREIGN PATENT DOCUMENTS

| CN | 108804112 A | 11/2018 |
| CN | 109951546 A | 6/2019 |
| CN | 110033244 A | 7/2019 |

(Continued)

OTHER PUBLICATIONS

Office Action issued by the Japanese Patent Office for Application No. 2021-025257, date of drafting Dec. 17, 2021.

(Continued)

*Primary Examiner* — Scott A. Waldron
(74) *Attorney, Agent, or Firm* — Banner & Witcoff, Ltd.

(57) ABSTRACT

A blockchain-based data processing method and apparatus, a device and a medium are provided, which are related to a blockchain technology. The method includes: acquiring a locally generated data processing transaction request; pre-executing the data processing transaction request, to determine a pre-execution result including write data; updating a data object in a local database according to the write data, and marking updated data of the data object as data with an unconfirmed state; encapsulating the pre-execution result into the request, and transmitting an encapsulated data processing transaction request to a blockchain network, to request other blockchain nodes to process it; and determining updated data associated with the encapsulated request as invalid data, in response to determining that the blockchain network refuses to execute it, or marking the updated data associated with the encapsulated request as data with a confirmed state, in response to determining that the blockchain network executes it.

20 Claims, 4 Drawing Sheets

(56) References Cited

U.S. PATENT DOCUMENTS

2020/0311053 A1* 10/2020 Verma ................ H04L 67/1097

FOREIGN PATENT DOCUMENTS

| | | | |
|---|---|---|---|
| CN | 110046523 A | | 7/2019 |
| CN | 110321219 A | * | 10/2019 |
| CN | 110321219 A | | 10/2019 |
| CN | 110659907 A | | 1/2020 |
| JP | 20018117287 A | | 7/2018 |
| JP | 2019029933 A | | 2/2019 |
| JP | 2020010267 A | | 1/2020 |
| WO | 2019/137567 A2 | | 7/2019 |
| WO | 2020/108288 A1 | | 6/2020 |

OTHER PUBLICATIONS

Extended European Search Report issued in EP Application No. 21158252.3, dated Jul. 2, 2021.
Jan. 5, 2023—(CN) First Search Report—App. No. 202010102672.9.
Jan. 11, 2023—(CN) First Office Action—App. No. 202010102672.9.

* cited by examiner

BLOCKCHAIN-BASED DATA PROCESSING METHOD AND APPARATUS, DEVICE, AND MEDIUM

CROSS-REFERENCE TO RELATED APPLICATIONS

This application claims priority to Chinese patent application, No. 202010102672.9, entitled "Blockchain-Based Data Processing Method and Apparatus, Device, and Medium", filed with the Chinese Patent Office on Feb. 19, 2020, which is hereby incorporated by reference in its entirety.

TECHNICAL FIELD

Embodiments of the present application relates to a field of computer technology, and particularly to a blockchain technology.

BACKGROUND

The blockchain technology is popularized rapidly, and has been applied to more and more scenarios to solve data processing and storage problems. One of typical application scenarios of the blockchain technology is the data summarization and storage for whole network convergence.

The so-called whole network convergence generally refers to an inclusion of a plurality of data centers in a whole network, and at each data center, there will exist needs of data addition, data deletion, data modification and data check. Within the scope of a whole network, data of respective data centers should be statistically summarized and stored. Taking a hospital system as an example, each hospital has its own data center, and data of a plurality of hospitals needs to be summarized, and sent to higher-level government agencies for further summarizing.

SUMMARY

A blockchain-based data processing method and apparatus, a device, and a medium are provided according to embodiments of the present application.

In a first aspect, an embodiment of the present application provides a blockchain-based data processing method, including:

acquiring a locally generated data processing transaction request;

pre-executing the data processing transaction request, to determine a pre-execution result including write data;

updating a data object in a local database according to the write data, and marking updated data of the data object as data with an unconfirmed state;

encapsulating the pre-execution result into the data processing transaction request, and transmitting an encapsulated data processing transaction request to a blockchain network, to request other blockchain nodes to process the encapsulated data processing transaction request; and determining updated data associated with the encapsulated data processing transaction request as invalid data, in response to determining that the blockchain network refuses to execute the encapsulated data processing transaction request, or marking the updated data associated with the encapsulated data processing transaction request as data with a confirmed state, in response to determining that the blockchain network executes the encapsulated data processing transaction request.

In a second aspect, an embodiment of the present application provides a blockchain-based data processing apparatus, including:

a data processing transaction request acquisition module, configured to acquire a locally generated data processing transaction request;

a data processing transaction request pre-execution module, configured to pre-execute the data processing transaction request, to determine a pre-execution result including write data;

an unconfirmed state marking module, configured to update a data object in a local database according to the write data, and mark updated data of the data object as data with an unconfirmed state;

a pre-execution result encapsulation module, configured to encapsulate the pre-execution result into the data processing transaction request, and transmit an encapsulated data processing transaction request to a blockchain network, to request other blockchain nodes to process the encapsulated data processing transaction request;

a first updated data processing module, configured to determine updated data associated with the encapsulated data processing transaction request as invalid data, in response to determining that the blockchain network refuses to execute the encapsulated data processing transaction request; and a second updated data processing module, configured to mark the updated data associated with the encapsulated data processing transaction request as data with a confirmed state, in response to determining that the blockchain network executes the encapsulated data processing transaction request.

In a third aspect, an embodiment of the present disclosure provides a computer device, including:

at least one processor; and a memory communicatively connected to the at least one processor, wherein the memory stores instructions executable by the at least one processor, the instructions are executed by the at least one processor to enable the at least one processor to perform a blockchain-based data processing method provided by embodiments in the first aspect.

In a fourth aspect, an embodiment of the present application provides a non-transitory computer readable storage medium for storing computer instructions, wherein the computer instructions, when executed by a computer, cause the computer to perform a blockchain-based data processing method provided by embodiments in the first aspect.

Other effects of above optional ways will be explained as follow in conjunction with specific embodiments.

BRIEF DESCRIPTION OF THE DRAWINGS

The accompanying drawings are provided for better understanding of the solution, rather than limiting the present application. In which.

DETAILED DESCRIPTION OF THE EMBODIMENTS

Exemplary embodiments of the present application are described below with reference to accompanying drawings, including various details of the embodiments of the present application to facilitate understanding, which should be considered as merely exemplary. Thus, it should be realized by those of ordinary skill in the art that various changes and modifications can be made to the embodiments described here without departing from the scope and spirit of the present application. Likewise, descriptions of well-known functions and structures are omitted in the following description for clarity and conciseness.

Embodiment 1

Figure 1:
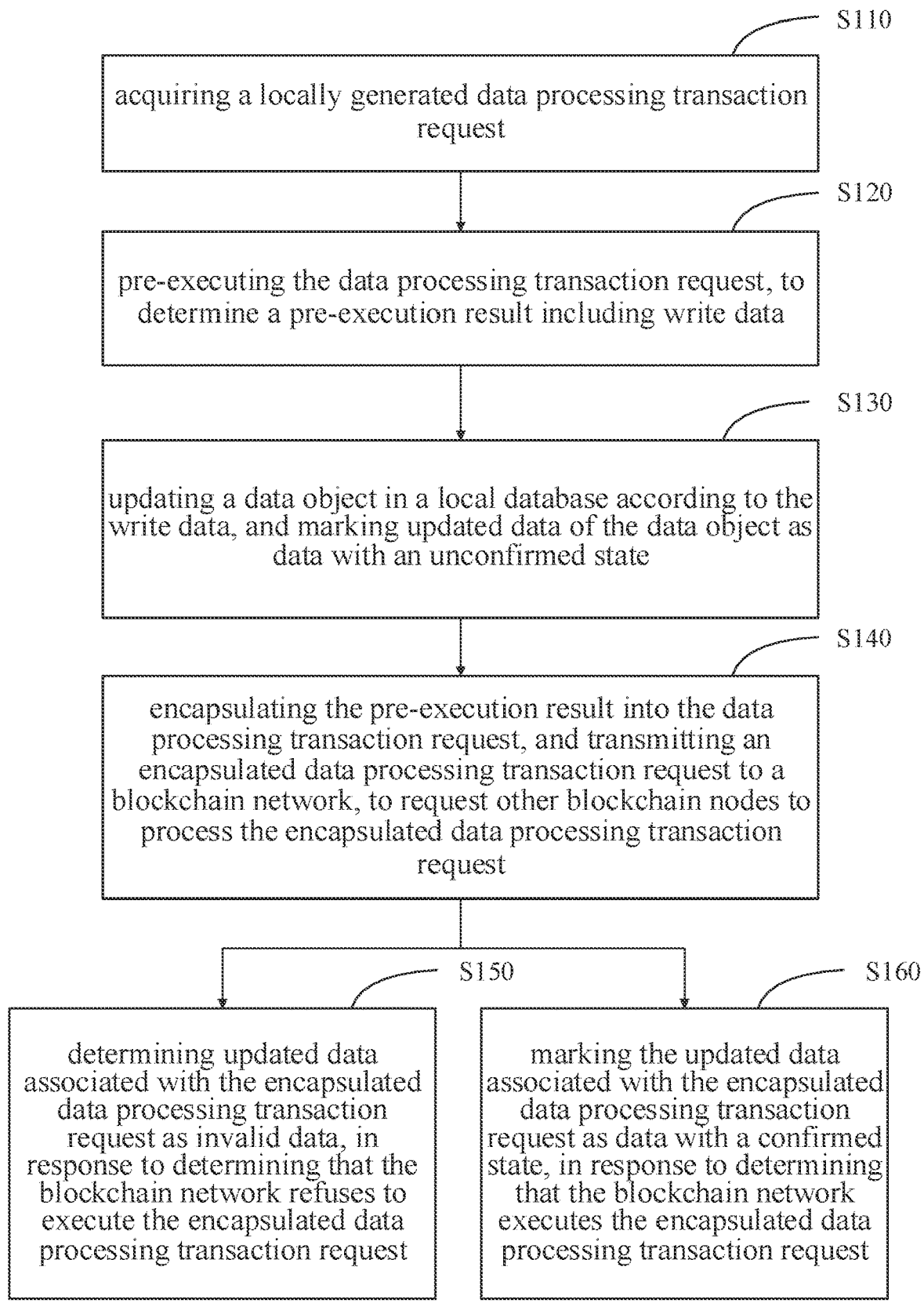
FIG. 1 is a flowchart showing a blockchain-based data processing method provided in Embodiment 1 of the present application.

FIG. 1 is a flowchart showing a blockchain-based data processing method provided in Embodiment 1 of the present application, and the embodiment of the present application is applicable to efficient data processing in a blockchain. The method may be performed by a blockchain-based data processing apparatus, which may be implemented by software and/or hardware and generally may be integrated in a computer device. The computer device may be a blockchain node device. Accordingly, as shown in FIG. 1, the method includes following operations:

S110: acquiring a locally generated data processing transaction request.

In which, a data processing transaction request may be a transaction request generated by a blockchain node to process data. Optionally, a blockchain node may be configured at a computer device or an electronic device of a data center such as a hospital data center and/or a toll station data center. The application scenario of a blockchain node is not limited herein.

In the embodiment of the present application, various data centers may participate in an operation of a blockchain network as blockchain nodes, to realize a whole network convergence of respective data centers through a blockchain technology. A blockchain node may generate a data processing transaction request for each data object in a blockchain network, data processing may include access operations such as data addition, data deletion, data modification, and data check.

Each data center has its own data management requirement, so data objects may be stored locally for quick query. For a blockchain network composed of data centers, each data center generally generates new data according to offline businesses. For example, a data center of a hospital generates information such as new cases, new drug consumptions, for which a data processing transaction request will be generated locally.

Data objects stored locally by one or more of blockchain nodes on demands may be the same as or be different from those stored locally by others of the blockchain nodes. For example, data centers of different hospitals may only be interested in patient information involved in their own hospitals, respectively, so they only store patient data objects related to their own hospitals. Data centers of different hospitals may also be interested in some data of other hospitals, such as drug stocks and blood stocks. All the information will be chained and stored as data objects, and may be summarized based on the information chained and stored. For example, drug stocks in all hospitals need to be summarized and counted, and new cases and new deaths in each hospital on a certain day need to be summarized and counted.

S120: pre-executing the data processing transaction request to determine a pre-execution result including write data.

In which, a pre-execution may be understood as local processing of a data processing transaction request by a blockchain node. A pre-execution result may be understood as a result of locally processing a data processing transaction request by a blockchain node. A pre-execution result usually includes a read operation on existing data objects, and a write operation on existing data objects or new data objects. A data object involved in a read operation is read data, and a data object involved in a write operation is write data.

Correspondingly, after acquiring a locally generated data processing transaction request, a blockchain node may call a corresponding smart contract to pre-execute the data processing transaction request, to obtain a pre-execution result including read data and write data.

S130: updating a data object in a local database according to the write data, and marking updated data of the data object as data with an unconfirmed state.

In which, an unconfirmed state may be a state type marked for data locally stored by a blockchain node.

In a traditional blockchain network, an execution result of a data processing transaction request cannot be chained unless being verified and confirmed by all the nodes, and an unchained data will not be updated to a local database. If a data processing transaction request cannot be processed and chained in time due to problems such as a network communication problem, a problem of concurrency quantity of transaction requests, such data cannot be used locally. For example, a data center of a hospital cannot provide the query of these unchained data to its internal staff, let along to external personnel. Therefore, the timeliness is poor.

In order to solve this problem, in an embodiment of the present application, after acquiring a pre-execution result of a data processing transaction request, a blockchain node may immediately update a data object in a local database according to write data in the pre-execution result. In a specific example, it is assumed that a data object is a total number of confirmed cases, with a corresponding value of 100. If write data in a pre-execution result indicates 5 newly confirmed cases, updating the data object in the local database according to the write data in the pre-execution result may be updating the total number of confirmed cases to 105.

It should be noted that a pre-execution result is only a local execution result of a blockchain node, and has not gained a consensus of other blockchain nodes, so its validity cannot be confirmed. However, in order to realize the functions of adding, deleting, modifying, and checking local data by a blockchain node, data object in the local database may be updated according to a pre-execution result, and updated data of the data object may be marked as data with an unconfirmed state, to determine that the updated data of the data object has not gained consensus. Data in a local database of a blockchain node may be queried and accessed, while it may be acquired whether a data object is in a confirmed state of being chained or in an unconfirmed state of not being chained.

S140: encapsulating the pre-execution result into the data processing transaction request, and transmitting an encapsulated data processing transaction request to a blockchain network, to request other blockchain nodes to process the encapsulated data processing transaction request.

Correspondingly, a blockchain node may encapsulate an acquired pre-execution result of a data processing transaction request into the data processing transaction request, and transmit an encapsulated data processing transaction request to a blockchain network, to request other blockchain nodes to process the data processing transaction request. After receiving the data processing transaction request, other blockchain nodes may also execute the received data processing transaction request, to complete a verification. An execution result can be chained if it is consistent with a pre-execution result.

S150: determining updated data associated with the encapsulated data processing transaction request as invalid data, in response to determining that the blockchain network refuses to execute the encapsulated data processing transaction request.

In an optional embodiment of the present application, determining that the blockchain network refuses to execute the encapsulated data processing transaction request may include receiving a notification of refusing to execute the encapsulated data processing transaction request fed back by one or more of the other blockchain nodes.

Various blockchain nodes in a blockchain network perform processing according to received data processing transaction requests, but processing results may fail to gain a consensus. If a processing result is conflicted with a pre-execution result included in a data processing transaction request, a notification of refusing to execute the data processing transaction request will be generated. Optionally, other blockchain nodes may feed notifications of refusing to execute a data processing transaction request back by means of unicast or broadcast.

It should be noted that in some cases, various blockchain nodes in a blockchain network perform processing according to received data processing transaction requests, and processing results gain a consensus, that is, other blockchain nodes do not feed any notification of refusing to execute the data processing transaction requests back, however, due to many factors, such as a message loss or delay caused by a poor network communication quality, the blockchain network does not generate any corresponding blocks or does not undergo a chaining operation within set time, it may be defaulted that the blockchain network refuses to execute the data processing transaction requests. That is, there may be many reasons which cause that a data processing transaction request is refused to be executed, to which no limitations are made herein.

In an embodiment of the present application, if a blockchain node determines that a blockchain network refuses to execute a data processing transaction request, a pre-execution result of the data processing transaction request is considered to be invalid, and updated data corresponding to the data processing transaction request may be determined as invalid data.

In an optional embodiment of the present application, determining the updated data associated with the encapsulated data processing transaction request as invalid data may include deleting the updated data associated with the encapsulated data processing transaction request, or marking the updated data associated with the encapsulated data processing transaction request as data with an invalid state. By invalidating updated data, that is, by performing an operation on invalid updated data, that is, by performing an invalidation operation thereon, error data may be screened/selected and processed, thereby improving data processing accuracy.

In an optional embodiment of the present application, after determining the updated data associated with the encapsulated data processing transaction request as invalid data, the method may further include: in response to determining that the local database includes other data with an unconfirmed state that depends on invalid data or current invalid data, determining the other data with the unconfirmed state as invalid data, and determining another data processing transaction request associated with the other data with the unconfirmed state as an invalid request.

It may be understood that there may be dependencies between data processing transaction requests. For example, a data processing transaction request 1 and a data processing transaction request 2 are both to calculate a total number of confirmed cases. After finishing processing of the data processing transaction request 1, a blockchain node needs to process the data processing transaction request 2 based on a processing result of the data processing transaction request 1. Therefore, the data processing transaction request 2 should depend on processed data of the data processing transaction request 1. In this case, if the processed data of the data processing transaction request 1 is invalid, i.e., it has not gained a consensus in the blockchain, the data in an unconfirmed state of the data processing transaction request 2 obtained based on the processed data of the data processing transaction request 1 is also invalid, it is necessary to determine the data in the unconfirmed state of the data processing transaction request 2 as invalid data, and determine the data processing transaction request 2 as an invalid request. The advantage of this setting is that it may effectively avoid the continuous influence of data with dependencies on subsequent data processing transaction requests, and prevent batch errors of local data of a blockchain node.

In an optional embodiment of the present application, after determining the updated data associated with the encapsulated data processing transaction request as invalid data, the method may further include discarding the encapsulated data processing transaction request, or generating an updated data processing transaction request according to the encapsulated data processing transaction request, and pre-executing the updated data processing transaction request.

Correspondingly, if it is determined that updated data associated with an encapsulated data processing transaction request is invalid, the data processing transaction request may be directly discarded. Alternatively, a new or updated data processing transaction request may be generated and pre-executed according to an encapsulated data processing transaction request, to ensure that a data processing transaction request is processed effectively and correctly.

In a specific example, it is assumed that a data object is a total number of confirmed cases, with a corresponding value of 100. An encapsulated data processing transaction request 1 may be "5 confirmed cases are added, please calculate a total number of the confirmed cases" (10 confirmed cases are added actually). The write data included in the pre-execution result of the encapsulated data processing transaction request 1 is that 5 confirmed cases are added (the actual write data should be that 10 confirmed cases are added). Updating the data object in the local database according to the write data in the pre-execution result may be updating the total number of the confirmed cases to be 105. In this case, the updated data of the data object is determined as invalid. The encapsulated data processing transaction request 1 may be discarded directly. Alternatively, according to actual content of the encapsulated data processing transaction request 1 "5 confirmed cases are added, please calculate a total number of the confirmed cases', a new/updated data processing transaction request 2 "10 confirmed cases are added, please calculate a total number of the confirmed cases" may be generated and pre-executed.

S160: marking the updated data associated with the encapsulated data processing transaction request as data with a confirmed state, in response to determining that the blockchain network executes the encapsulated data processing transaction request.

In the embodiment of the present application, if a blockchain node determines that a blockchain network executes/has executed the encapsulated data processing transaction request, it indicates that a pre-execution result is confirmed and chained, the updated data may be marked as data with a confirmed state. The marked updated data with a confirmed state may be the same as processed data corresponding to the encapsulated data processing transaction request.

In an optional embodiment of the present application, a blockchain-based data processing method may further include performing response processing based on the data with the confirmed state and the data with the unconfirmed state in the local database, in response to receiving a data access request.

In which, a data access request may be a request sent by any other blockchain node or an internal user of a blockchain node, to access data stored by a blockchain node in a local database.

In an embodiment of the present application, the locally generated data processing transaction request is a data write processing transaction request, and data objects targeted by blockchain nodes have intersections.

By limiting that data objects targeted by one or more of a plurality of blockchain nodes may be the same as data objects targeted by others of the blockchain nodes, relations between data processing transaction requests of the blockchain nodes may be established, thereby achieving whole network convergence of a blockchain network.

In an embodiment of the present application, an access query function may be provided for data with a confirmed state and data with an unconfirmed state stored by a blockchain node in a local database, to realize data sharing and intercommunication.

According to an embodiment of the present application, an acquired data processing transaction request is pre-executed, to obtain a pre-execution result including read data and write data, a data object in a local database is updated according to the write data, updated data of the data object is marked as data with an unconfirmed state, a pre-execution result is encapsulated into the data processing transaction request, an encapsulated data processing transaction request is transmitted to a blockchain network, to request other blockchain nodes to process the encapsulated data processing transaction request, and according to a processing result, updated data associated with the encapsulated data processing transaction request is determined as invalid data, or marked as data with a confirmed state, so that the problem of a poor timeliness of data processing may be solved as the existing blockchain technology is applied to a data summarization system, thereby improving the timeliness of data processing in a data summarization system for whole network convergence.

Embodiment 2

Figure 2:
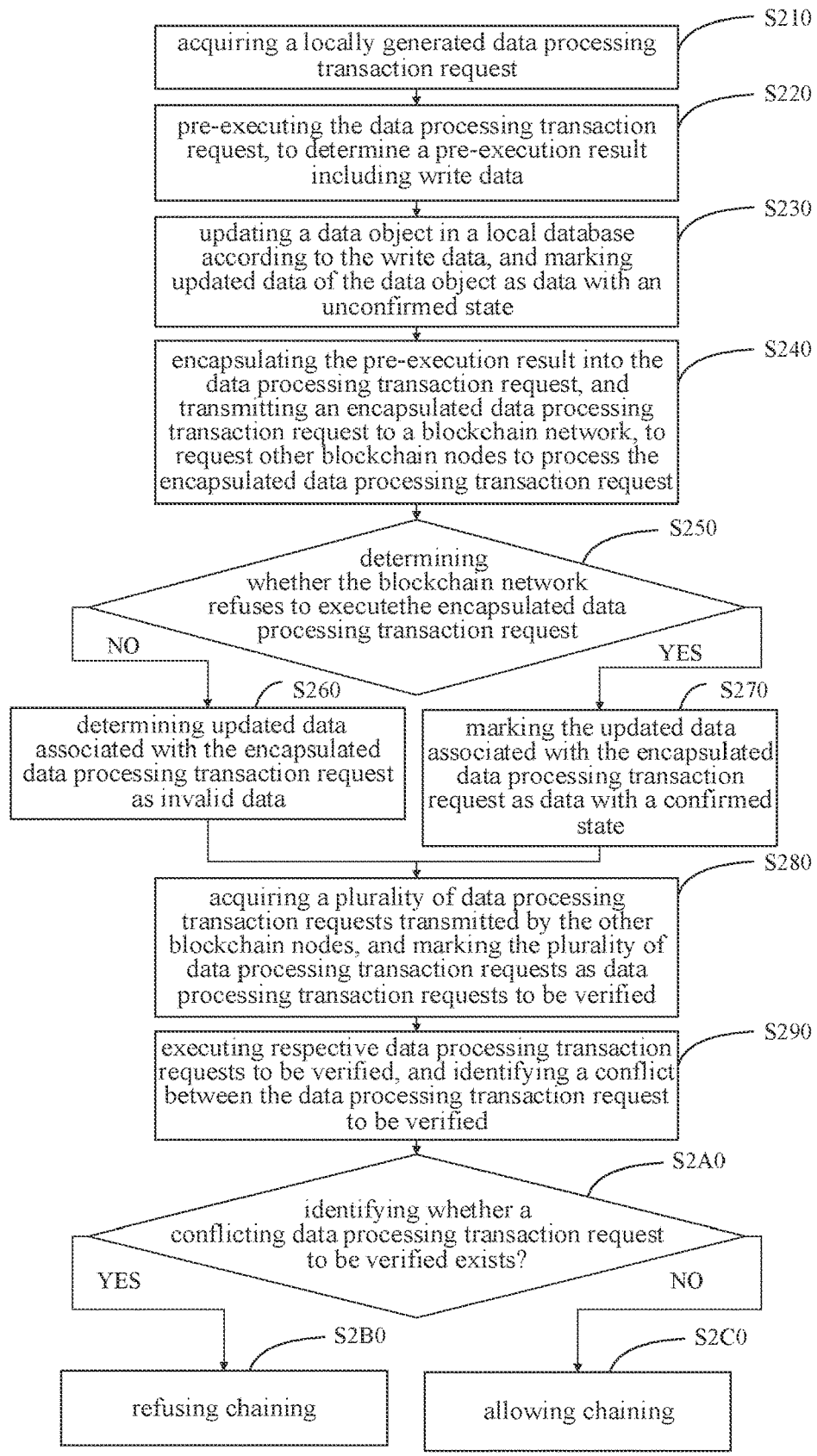
FIG. 2 is a flowchart showing a blockchain-based data processing method provided in Embodiment 2 of the present application.

FIG. 2 is a flowchart showing a blockchain-based data processing method provided in Embodiment 2 of the present application. The embodiment of the present application is optimized and improved based on the technical solutions of the above embodiment, and provides a processing mode for a conflicting data processing transaction request in a blockchain.

As shown in FIG. 2, a blockchain-based data processing method includes:

S210: acquiring a locally generated data processing transaction request.

S220: pre-executing the data processing transaction request, to determine a pre-execution result including write data.

S230: updating a data object in a local database according to the write data, and marking updated data of the data object as data with an unconfirmed state.

S240: encapsulating the pre-execution result into the data processing transaction request, and transmitting an encapsulated data processing transaction request to a blockchain network to request other blockchain nodes to process the encapsulated data processing transaction request.

S250: determining whether the blockchain network refuses to execute the encapsulated data processing transaction request, and performing S260, in response to determining that the blockchain network refuses to execute the encapsulated data processing transaction request; or performing S270, in response to determining that the blockchain network executes the encapsulated data processing transaction request.

S260: determining updated data associated with the encapsulated data processing transaction request as invalid data.

S270: marking the updated data associated with the encapsulated data processing transaction request as data with a confirmed state.

S280: acquiring a plurality of data processing transaction requests transmitted by the other blockchain nodes, and marking the plurality of data processing transaction requests as data processing transaction requests to be verified.

In the embodiment of the present application, a blockchain node may locally initiate a transaction request, or acquire transaction requests initiated by other nodes and verify and confirm the transaction requests. The transaction requests acquired from other nodes are marked as data processing transaction requests to be verified. Generally, transaction requests are processed by a current block output node, packaged into blocks, and broadcast to other nodes which perform a verification according to received transaction requests, to verify correctness of the blocks.

S290: executing respective data processing transaction requests to be verified, and identifying a conflict between the data processing transaction requests to be verified.

It should be understood that in case that data objects are simultaneously updated by multiple parties, due to the influence of the network communication quality and other factors, there may be a conflict between data processing transaction requests. It is mainly because conflicts will occur when multiple parties simultaneously initiate write operations on a same data object.

Accordingly, after having block processing authority, a blockchain node may adopt a smart contract to execute each of received data processing transaction requests to be verified, and identify conflicts therebetween.

In an optional embodiment of the present application, executing the respective data processing transaction requests to be verified, and identifying the conflict between the data processing transaction requests to be verified may include: executing the respective data processing transaction requests to be verified seriatim in a set order; and determining that a currently executed data processing transaction request to be verified is a conflicting data processing transaction request, in response to identifying that a conflict exists between the currently executed data processing transaction request to be verified and a historically executed data processing transaction request to be verified.

In which, the setting sequence may be a time order of receiving data processing transaction requests to be verified, to which no limitations are made herein. A historically executed data processing transaction request to be verified may be any data processing transaction request to be verified received before a currently executed data processing transaction request to be verified.

In an embodiment of the present application, respective data processing transaction requests to be verified may be executed seriatim in a set order. It may be determined that a currently executed data processing transaction request to be verified is a conflicting data processing transaction request, in response to identifying that a conflict exists between the currently executed data processing transaction request to be verified and a historically executed data processing transaction request to be verified, to effectively identify whether there is a conflict between data processing transaction requests to be verified.

In a specific example, a data object "a total number of confirmed cases" needs to be summarized and reported from district hospitals 1 and 2. Assuming that a data center of the district hospital 1 generates a data processing transaction request 1 "5 confirmed cases are added, please calculate a total number of the confirmed cases" for a data object with a version number of P, and a data center of the district hospital 2 generates a data processing transaction request 2 "3 confirmed cases are added, please calculate a total number of the confirmed cases" for the data object with the version number of P. But the data center of the district hospital 2 is influenced by the network communication quality, which leads to a delay in sending the data processing transaction request 2. The blockchain node firstly receives and executes the data processing transaction request 1. At this time, the version number of the data object is changed to T, and then the data processing transaction request 2 is received. However, the data object has been updated, and there is a conflict between the data processing transaction request 1 and the data processing transaction request 2.

It should be noted that identifying whether there is a conflict between data processing transaction requests to be verified is not limited to data processing transaction request to be verified corresponding to a block which currently performs processing. In case that a block is just generated for a short time, a data processing transaction request to be verified included in the block which currently performs processing may also conflict with a data processing transaction request to be verified in a generated block. For example, a block 1 chains a data object a, with a value of 10, a version number of A, and a block identifier of 1. A block 2 updates the data object a, with a value of 20, a version number of B, and a block identifier of 2. At this time, if a data processing transaction request to be verified in a block 3 requests to modify the data of the data object a with the version number of A, the data processing transaction request to be verified conflicts with the data processing transaction request to be verified for updating the data object a in the block 2.

In an optional embodiment of the present application, executing the respective data processing transaction requests to be verified, and identifying a conflict between the data processing transaction requests to be verified may further include: identifying a dependency relationship according to pre-execution results of the respective data processing transaction requests to be verified, and performing topological sorting according to an identifying result: and in response to identifying that a conflict exists between two or more of the data processing transaction requests to be verified during the topological sorting, accepting one of the two or more data processing transaction requests to be verified, and determining that other data processing transaction requests to be verified of the two or more data processing transaction requests to be verified are conflicting data processing transaction requests, to effectively identify whether there is a conflict between data processing transaction requests to be verified.

In which, a topological sorting may be an execution order for transaction requests determined according to a write data dependency relation between pre-execution results.

In an embodiment of the present application, in case of identifying a conflict between data processing transaction requests to be verified, a blockchain node may also identify a dependency relationship according to pre-execution results of all of data processing transaction requests to be verified received within a set time period, and perform topological sorting according to an identifying result, where the set time period may be set on demand, such as a time period corresponding to block generation time. In the topological sorting, a blockchain node may accept one of data processing transaction requests to be verified and determine that other data processing transaction requests to be verified of the two or more data processing transaction requests to be verified are conflicting data processing transaction requests, if it is found that there is a conflict between the two and more of data processing transaction requests to be verified.

In an optional embodiment of the present application, executing the respective data processing transaction requests to be verified, and identifying the conflict between the data processing transaction requests to be verified may include: identifying a dependency relationship according to pre-execution results of the respective data processing transaction requests to be verified, and performing topological sorting according to an identifying result; executing the respective data processing transaction requests to be verified according to a topological sorting result; and determining that a currently executed data processing transaction request to be verified is a conflicting data processing transaction request, in response to identifying that a conflict exists between the currently executed data processing transaction request to be verified and a historically executed data processing transaction request to be verified, to effectively identify whether there is a conflict between data processing transaction requests to be verified.

In an embodiment of the present application, when identifying a conflict between data processing transaction requests to be verified, a blockchain node may also identify a dependency relationship according to pre-execution results of all of data processing transaction requests to be verified received within a set time period, and perform topological sorting according to an identifying result, where the set time period may be set on demand, such as a time period corresponding to block generation time. Next, the data processing transaction requests to be verified may be executed according to a topological sorting result. For example, the respective data processing transaction requests to be verified obtained after the topological sorting may be executed seriatim in a set order. It is determined that a currently executed data processing transaction request to be verified is a conflicting data processing transaction request, in case that there is a conflict between the currently executed data processing transaction request to be verified and a historically executed data processing transaction request to be verified.

It should be noted that, after the respective data processing transaction requests to be verified are executed according to a topological sorting result, although it is determined that the currently executed data processing transaction request to be verified is a conflicting data processing transaction request, a data writing result of the update date associated with the currently executed data processing transaction request to be verified is consistent with a data writing result of the update date associated with the historically executed data processing transaction request to be verified, that is, the data writing result of the update date associated with the currently executed data processing transaction request to be verified is still correct, the currently executed data processing transaction request to be verified may not be refused. For example, although two data processing transaction requests both change a drug price into RMB 100 yuan, i.e., the same data object is modified, it may be considered that no conflict occurs because the modification results are the same.

S2A0: identifying whether a conflicting data processing transaction request to be verified exists; performing S2B0, in response to determining that a conflicting data processing transaction request to be verified is identified; or performing S2C0, in response to determining that a conflicting data processing transaction request to be verified is not identified.

S2B0: refusing chaining.

S2C0: allowing chaining.

Accordingly, a blockchain node may refuse chaining, in response to identifying a conflicting data processing transaction request, to ensure the accuracy of block data. In embodiments of the present application, refusing chaining may be understood as refusing to connect a conflicting data processing transaction request to be verified into a blockchain, and allowing chaining may be understood as allowing connecting a conflicting data processing transaction request to be verified into a blockchain.

By adopting the above technical scheme, a conflict between data processing transaction requests may be identified, and an identified conflicting data processing transaction request may be refused to connect into a blockchain, so that the accuracy of block data may be ensured.

Embodiment 3

Figure 3:
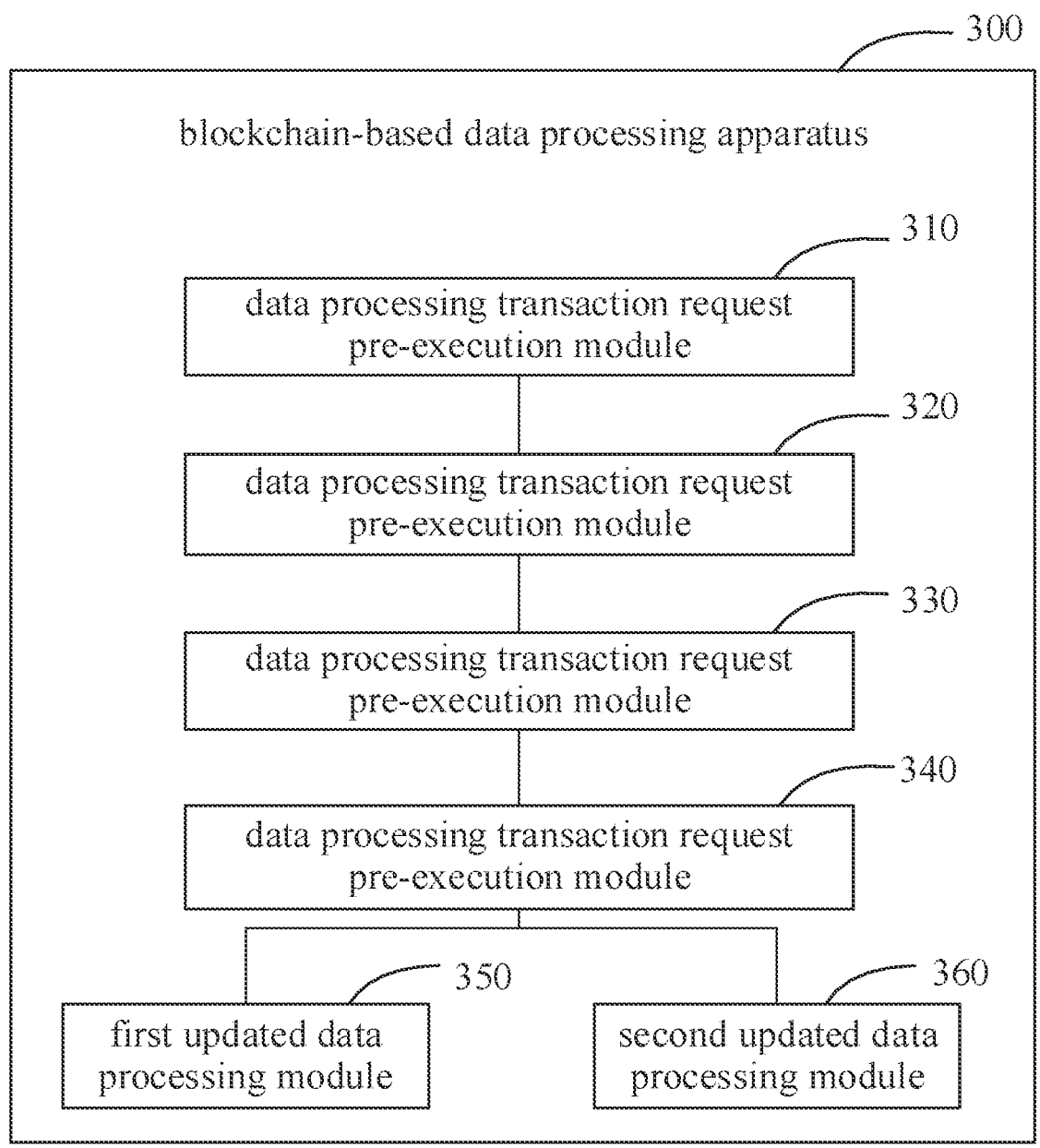
FIG. 3 is a structural diagram showing a blockchain-based data processing apparatus provided in Embodiment 3 of the present application.

FIG. 3 is a structural diagram showing a blockchain-based data processing apparatus provided in Embodiment 3 of the present application, and the apparatus is configured at a blockchain node. The embodiment of the present application may be applicable to efficient data processing in a blockchain. The apparatus may be implemented by software and/or hardware and specifically configured in a computer device. The computer device may be a blockchain node device.

As shown in FIG. 3, a blockchain-based data processing apparatus 300 may include: a data processing transaction request acquisition module 310, a data processing transaction request pre-execution module 320, an unconfirmed state marking module 330, a pre-execution result encapsulation module 340, a first updated data processing module 350, and a second updated data processing module 360. In which, the data processing transaction request acquisition module 310 is configured to acquire a locally generated data processing transaction request;

the data processing transaction request pre-execution module 320 is configured to pre-execute the data processing transaction request, to determine a pre-execution result including read data and write data;

the unconfirmed state marking module 330 is configured to update a data object in a local database according to the write data, and mark updated data of the data object as data with an unconfirmed state;

the pre-execution result encapsulation module 340 is configured to encapsulate the pre-execution result into the data processing transaction request, and transmit an encapsulated data processing transaction request to a blockchain network, to request other blockchain nodes to process the encapsulated data processing transaction request;

the first updated data processing module 350 is configured to determine updated data associated with the encapsulated data processing transaction request as invalid data, in response to determining that the blockchain network refuses to execute the encapsulated data processing transaction request;

the second updated data processing module 360 is configured to mark the updated data associated with the encapsulated data processing transaction request as data with a confirmed state, in response to determining that the blockchain network executes the encapsulated data processing transaction request.

According to an embodiment of the present application, an acquired data processing transaction request is pre-executed, so that a pre-execution result including read data and write data may be obtained, a data object in a local database is updated according to write data, updated data of the data object is marked as data with an unconfirmed state, a pre-execution result is encapsulated into a data processing transaction request, and an encapsulated data processing transaction request is transmitted to a blockchain network, to request other blockchain nodes to process the encapsulated data processing transaction request, and according to a processing result, updated data associated with the encapsulated data processing transaction request is determined as invalid data or marked as data with a confirmed state, so that the problem of a poor timeliness of data processing may be solved as the existing blockchain technology is applied to a data summarization system, thereby improving the timeliness of data processing in a data summarization system for whole network convergence.

Optionally, the first updated data processing module 350 may include a notification receiving unit configured to receive a notification of refusing to execute the encapsulated data processing transaction request fed back by one of more of the other blockchain nodes.

Optionally, the first updated data processing module 350 may further include a first updated data processing unit configured to delete the updated data associated with the encapsulated data processing transaction request, or mark the updated data associated with the encapsulated data processing transaction request as data with an invalid state.

Optionally, the blockchain-based data processing apparatus further includes a first data request processing module configured to, in response to determining that the local database includes other data with an unconfirmed state that depends on the invalid data, determine the other data with the unconfirmed state as invalid data, and determine another data processing transaction request associated with the other data with the unconfirmed state as an invalid request.

Optionally, the blockchain-based data processing apparatus may further include a second data request processing module configured to discard the encapsulated data processing transaction request, or generate an updated data processing transaction request according to the encapsulated data processing transaction request, and pre-executing the updated data processing transaction request.

Optionally, the blockchain-based data processing apparatus may further include a data access request response processing module configured to perform response processing based on the data with the confirmed state and the data with the unconfirmed state in the local database, in response to receiving a data access request.

Optionally, the blockchain-based data processing apparatus may further include: a data processing transaction request to be verified acquisition module configured to acquire a plurality of data processing transaction requests transmitted by the other blockchain nodes, and marking the plurality of data processing transaction requests as data processing transaction requests to be verified; a conflict identification module configured to execute respective data processing transaction requests to be verified, and identify a conflict between the data processing transaction requests to be verified; and a chaining processing module configured to refuse chaining, in response to identifying the conflicting data processing transaction request to be verified.

Optionally, the conflict identifying module may include: a first data processing transaction request to be verified execution unit configured to execute the respective data processing transaction requests to be verified seriatim in a set order: and a first conflict identifying unit configured to determine that a currently executed data processing transaction request to be verified is a conflicting data processing transaction request, in response to identifying that a conflict exists between the currently executed data processing transaction request to be verified and a historically executed data processing transaction request to be verified.

Optionally, the conflict identifying module may include: a first pre-execution result identifying unit configured to identify a dependency relationship according to pre-execution results of the respective data processing transaction requests to be verified, and perform topological sorting according to an identifying result; and a second conflict identifying unit configured to, in response to identifying that a conflict exists between two or more of the data processing transaction requests to be verified during the topological sorting, accept one of the two or more data processing transaction requests to be verified, and determine that other data processing transaction requests to be verified of the two or more data processing transaction requests to be verified are conflicting data processing transaction requests.

Optionally, the conflict identifying module may include: a second pre-execution result identifying unit configured to identify a dependency relationship according to pre-execution results of the respective data processing transaction requests to be verified, and perform topological sorting according to an identifying result; a second conflict identifying unit configured to execute the respective data processing transaction requests to be verified according to a topological sorting result; and a third conflict identifying unit configured to determine that a currently executed data processing transaction request to be verified is the conflicting data processing transaction request, in response to identifying that a conflict exists between the currently executed data processing transaction request to be verified and a historically executed data processing transaction request to be verified.

Optionally, the locally generated data processing transaction request is a data write processing transaction request, and data objects targeted by one or more of the blockchain nodes can be the same as data objects targeted by others of the blockchain nodes.

Optionally, the blockchain nodes may be configured in a data center of a hospital and/or a data center of a toll station.

The blockchain-based data processing apparatus may perform a blockchain-based data processing method provided by any embodiment of the present application, and has corresponding functional modules and beneficial effects of the performance of the blockchain-based data processing method.

Embodiment 4

According to embodiments of the present application, the present application may further provide a computer device and a readable storage medium.

Figure 4:
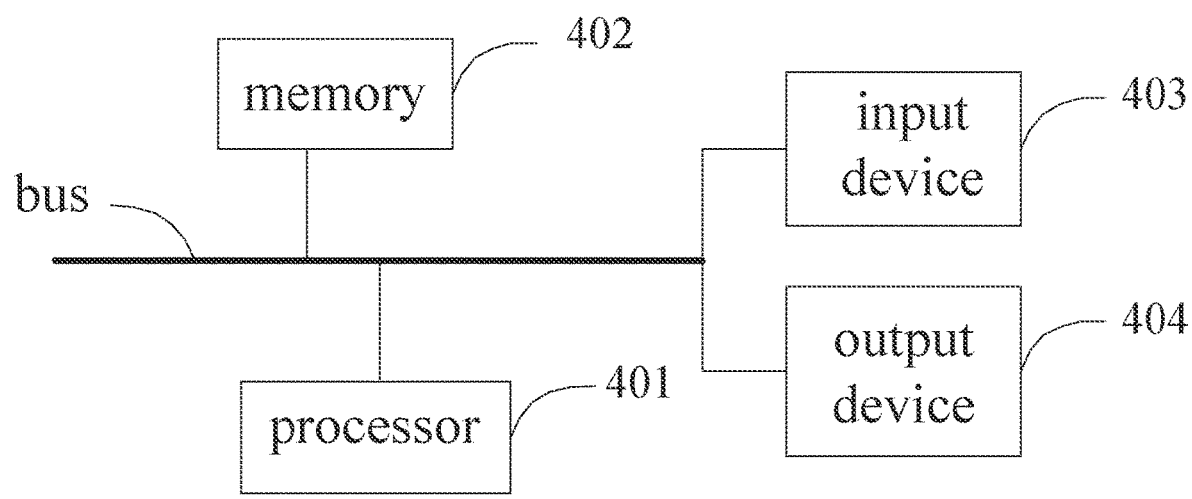
FIG. 4 is a block diagram showing a computer device for implementing a blockchain-based data processing method according to an embodiment of the present application.

FIG. 4 is a block diagram showing a computer device for implementing a blockchain-based data processing method according to an embodiment of the present application. A computer device is intended to represent various forms of digital computers, such as a laptop computer, a desktop computer, a workbench, a personal digital assistant, a server, a blade server, a mainframe computer, and other suitable computers. A computer device may also represent various forms of mobile devices, such as a personal digital assistant, a cellular phone, a smart phone, a wearable device, and other similar computing devices. The components illustrated herein, connections and relationships therebetween, and functions thereof are merely examples, and are not intended to limit the implementation of the present application described and/or claimed herein.

As shown in FIG. 4, a computer device may include: one or more processors 401, a memory 402, and interfaces for connecting various components, including a high-speed interface and a low-speed interface. The various components are connected to each other using different buses and may be installed on a common motherboard or installed in other ways as needed. The processor may process instructions executed in the computer device, including instructions stored in or on the memory to display graphic information of a Graphical User Interface (GUI) on an external input/output device (e.g., a display device coupled to an interface). In other embodiments, if necessary, a plurality of processors and/or a plurality of buses may be used together with a plurality of memories. Similarly, a plurality of computer devices may be connected, each providing some necessary operations (e.g., acting as a server array, a group of blade servers, or a multi-processor system). In FIG. 4, one processor 401 is taken as an example.

The memory 402 is a non-transitory computer-readable storage medium provided by the present application. The memory stores instructions executable by at least one processor, so that the at least one processor may perform the blockchain-based data processing method provided by the present application. The non-transitory computer-readable storage medium of the present application stores computer instructions, which are used to cause the computer to perform the blockchain-based data processing method provided by the present application.

As a non-transitory computer readable storage medium, the memory 402 may be configured to store non-transitory software programs, non-transitory computer executable programs and modules, such as program instructions/modules corresponding to the blockchain-based data processing method in embodiments of the present application (e.g., the data processing transaction request acquisition module 310, the data processing transaction request pre-execution module 320, the unconfirmed state marking module 330, the pre-execution result encapsulation module 340, the first updated data processing module 350 and the second updated data processing module 360 as shown in FIG. 3). The processor 401 executes various functional applications and data processing of the computer device by running the non-transitory software programs, instructions and modules stored in the memory 402, thereby realizing the blockchain-based data processing method in above method embodiments.

The memory 402 may comprise a program storage area and a data storage area, where the program storage area may store an operating system, and application programs required by at least one function; and the data storage area may store data created according to the use of the computer device for implementing the blockchain-based data processing method. In addition, the memory 402 may include a high-speed random-access memory, and may also include a non-transitory memory, such as at least one magnetic disk memory device, a flash memory device, or any other non-transitory solid memory device. In some embodiments, the memory 402 optionally comprises memories remotely located relative to the processor 401, and these remote memories may be connected to the computer device for implementing the blockchain-based data processing method through a network. Examples of the network include, but are not limited to, the Internet, an intranet, a local area network, a mobile communication network and combinations thereof.

The computer device for implementing the blockchain-based data processing method may further include input device 403 and output device 404. The processor 401, the memory 402, the input device 403, and the output device 404 may be connected by buses or in other ways. In FIG. 4, the connection through a bus is taken as an example.

The input device 403, such as a touch screen, a keypad, a mouse, a trackpad, a touchpad, an indication rod, one or more mouse buttons, a trackball, a joystick, may receive input digitals or character information, and generate key signal inputs related to user settings and a function control of the computer device for implementing the blockchain-based data processing method. The output device 404 may include a display apparatus, an auxiliary lighting device (e.g., a light-emitting diode (LED)), a haptic feedback apparatus (e.g., a vibration motor), etc. The display device may include, but is not limited to, a liquid crystal display (LCD), an LED display, and a plasma display. In some embodiments, the display apparatus may be a touch screen.

Various embodiments of the systems and techniques described herein may be implemented in digital electronic circuit systems, integrated circuit systems, application specific integrated circuits (ASICs), computer hardware, firmware, software, and/or combination thereof. These various embodiments may include: implementations in one or more computer programs which may be executed and/or interpreted on a programmable system that includes at least one programmable processor, which may be a dedicated or general-purpose programmable processor that may receive data and instructions from a storage system, at least one input device, and at least one output device, and transmit the data and instructions to the storage system, the at least one input device, and the at least one output device.

These computer programs, also called as programs, software, software applications, or codes, may include machine instructions of programmable processors, and these computer programs may be implemented using a high-level process and/or object-oriented programming language, and/or an assembly/machine language. As used herein, the terms "machine-readable medium" and "computer readable medium" refer to any computer program product, apparatus, and/or device, for example, a magnetic disk, an optical disk, a memory, a programmable logic device (PLD), used to provide machine instructions and/or data to a programmable processor, including the machine-readable medium that receives machine instructions as machine readable signals. The term "machine-readable signal" refers to any signal used to provide machine instructions and/or data to the programmable processor.

In order to provide interactions with a user, the system and technology described herein may be implemented on a computer which has: a display device, for example a cathode ray tube (CRT) or an LCD monitor, for displaying information to the user; and a keyboard and pointing device, for example a mouse or a trackball, through which the user may provide input to the computer. Other kinds of devices may also be used to provide interactions with a user; for example, the feedback provided to a user may be any form of sensory feedback, for example, visual feedback, auditory feedback, or tactile feedback; and input from a user may be received using any form, including acoustic input, voice input, or tactile input.

The systems and techniques described herein may be implemented in a computing system (for example, as a data server) that includes back-end components, or be implemented in a computing system (for example, an application server) that includes middleware components, or be implemented in a computing system (for example, a user computer with a graphical user interface or a web browser through which the user may interact with the implementation of the systems and technologies described herein) that includes front-end components, or be implemented in a computing system that includes any combination of such back-end components, intermediate components, or front-end components. The components of the system may be interconnected by any form or medium of digital data communication, for example, a communication network. Examples of communication networks include a Local Area Network (LAN), a Wide Area Network (WAN), the Internet and a blockchain network.

A computer system may include a client and a server. The client and the server are generally remote from each other and typically interact through a communication network. The client-server relationship is generated by computer programs that run on respective computers and have a client-server relationship with each other.

According to embodiments of the present application, an acquired data processing transaction request is pre-executed, so that a pre-execution result including read data and write data may be obtained, a data object in a local database is updated according to write data, updated data of the data object is marked as data with an unconfirmed state, a pre-execution result is encapsulated into a data processing transaction request, and an encapsulated data processing transaction request is transmitted to a blockchain network, to request other blockchain nodes to process the encapsulated data processing transaction request, and according to a processing result, updated data associated with the encapsulated data processing transaction request is determined as invalid data or marked as data with a confirmed state, so that the problem of a poor timeliness of data processing may be solved as the existing blockchain technology is applied to a data summarization system, thereby improving the timeliness of data processing in a data summarization system for whole network convergence.

It should be understood that various forms of processes shown above may be used to reorder, add, or delete steps. For example, respective steps described in the present application may be executed in parallel, or may be executed sequentially, or may be executed in a different order, as long as the desired result of the technical solution disclosed in the present application can be achieved, to which no limitation is made herein.

The above specific embodiments do not constitute a limitation on the protection scope of the present application. It should be understood by those skilled in the art that various modifications, combinations, sub-combinations, and substitutions may be made according to design requirements and other factors. Any modification, equivalent replacement, and improvement, and the like made within the spirit and principle of the present application shall be fall in the protection scope of the present application.

What is claimed is:

1. A blockchain-based data processing method performed by a blockchain node, implemented by circuits for implementing functions, comprising:
   acquiring a locally generated data processing transaction request from the blockchain node;
   pre-executing the data processing transaction request, to determine a pre-execution result including write data;
   updating a data object in a local database according to the write data, and marking updated data of the data object as data with an unconfirmed state, before a consensus of other blockchain nodes is gained;
   encapsulating the pre-execution result into the data processing transaction request, and transmitting an encapsulated data processing transaction request to a blockchain network, to request other blockchain nodes to process the encapsulated data processing transaction request, wherein in the process of processing the data processing transaction request by other blockchain nodes, executing the data processing transaction request to acquire at least one execution result, wherein each of the at least one execution result is used to be verified if it is consistent with the pre-execution result; and
   determining updated data associated with the encapsulated data processing transaction request as invalid data, in response to determining that the blockchain network refuses to execute the encapsulated data processing transaction request, or
   marking the updated data associated with the encapsulated data processing transaction request as data with a confirmed state, in response to determining that the blockchain network executes the encapsulated data processing transaction request.

2. The blockchain-based data processing method according to claim 1, wherein determining that the blockchain network refuses to execute the encapsulated data processing transaction request comprises:
   receiving a notification of refusing to execute the encapsulated data processing transaction request fed back by one or more of the other blockchain nodes.

3. The blockchain-based data processing method according to claim 1, wherein determining the updated data associated with the encapsulated data processing transaction request as invalid data comprises:
   deleting the updated data associated with the encapsulated data processing transaction request, or marking the updated data associated with the encapsulated data processing transaction request as data with an invalid state.

4. The blockchain-based data processing method according to claim 1, wherein after determining the updated data associated with the encapsulated data processing transaction request as invalid data, the method further comprises:
   in response to determining that the local database includes other data with an unconfirmed state that depends on the invalid data, determining the other data with the unconfirmed state as invalid data, and determining another data processing transaction request associated with the other data with the unconfirmed state as an invalid request.

5. The blockchain-based data processing method according to claim 1, wherein after determining the updated data associated with the encapsulated data processing transaction request as invalid data, the method further comprises:
   discarding the encapsulated data processing transaction request, or
   generating an updated data processing transaction request according to the encapsulated data processing transaction request, and pre-executing the updated data processing transaction request.

6. The blockchain-based data processing method according to claim 1, further comprising:
   performing response processing based on the data with the confirmed state and the data with the unconfirmed state in the local database, in response to receiving a data access request.

7. The blockchain-based data processing method according to claim 1, further comprising:
   acquiring a plurality of data processing transaction requests transmitted by the other blockchain nodes, and marking the plurality of data processing transaction requests as data processing transaction requests to be verified;
   executing respective data processing transaction requests to be verified, and identifying a conflict between the data processing transaction requests to be verified; and
   refusing chaining, in response to identifying the conflicting data processing transaction request to be verified.

8. The blockchain-based data processing method according to claim 7, wherein executing the respective data processing transaction requests to be verified, and identifying the conflict between the data processing transaction requests to be verified comprises:
   executing the respective data processing transaction requests to be verified seriatim in a set order; and
   determining that a currently executed data processing transaction request to be verified is a conflicting data processing transaction request, in response to identifying that a conflict exists between the currently executed data processing transaction request to be verified and a historically executed data processing transaction request to be verified.

9. The blockchain-based data processing method according to claim 7, wherein executing the respective data processing transaction requests to be verified, and identifying a conflict between the data processing transaction requests to be verified further comprises:
   identifying a dependency relationship according to pre-execution results of the respective data processing transaction requests to be verified, and performing topological sorting according to an identifying result; and in response to identifying that a conflict exists between two or more of the data processing transaction requests to be verified during the topological sorting, accepting one of the two or more data processing transaction requests to be verified, and determining that other data processing transaction requests to be verified of the two or more data processing transaction requests to be verified are conflicting data processing transaction requests.

10. The blockchain-based data processing method according to claim 7, wherein executing the respective data processing transaction requests to be verified, and identifying the conflict between the data processing transaction requests to be verified further comprises:
identifying a dependency relationship according to pre-execution results of the respective data processing transaction requests to be verified, and performing topological sorting according to an identifying result;
executing the respective data processing transaction requests to be verified according to a topological sorting result; and
determining that a currently executed data processing transaction request to be verified is a conflicting data processing transaction request, in response to identifying that a conflict exists between the currently executed data processing transaction request to be verified and a historically executed data processing transaction request to be verified.

11. The blockchain-based data processing method according to claim 1, wherein the locally generated data processing transaction request is a data write processing transaction request, and data objects targeted by one or more of the blockchain nodes can be the same as data objects targeted by others of the blockchain nodes.

12. The blockchain-based data processing method according to claim 11, wherein the blockchain nodes are configured in a data center of a hospital and/or a data center of a toll station.

13. A blockchain-based data processing apparatus arranged at a blockchain node, implemented by circuits for implementing functions, comprising:
at least one processor; and
a memory communicatively connected to the at least one processor, wherein
the memory stores instructions executable by the at least one processor, the instructions are executed by the at least one processor to enable the at least one processor to:
acquire a locally generated data processing transaction request;
pre-execute the data processing transaction request, to determine a pre-execution result including write data;
update a data object in a local database according to the write data, and mark updated data of the data object as data with an unconfirmed state, before a consensus of other blockchain nodes is gained;
encapsulate the pre-execution result into the data processing transaction request, and transmit an encapsulated data processing transaction request to a blockchain network, to request other blockchain nodes to process the encapsulated data processing transaction request, wherein in the process of processing the data processing transaction request by other blockchain nodes, execute the data processing transaction request to acquire at least one execution result, wherein each of the at least one execution result is used to be verified if it is consistent with the pre-execution result; and
determine updated data associated with the encapsulated data processing transaction request as invalid data, in response to determining that the blockchain network refuses to execute the encapsulated data processing transaction request; or
mark the updated data associated with the encapsulated data processing transaction request as data with a confirmed state, in response to determining that the blockchain network executes the encapsulated data processing transaction request.

14. The blockchain-based data processing apparatus according to claim 13, wherein the instructions are executed by the at least one processor to enable the at least one processor to:
receive a notification of refusing to execute the encapsulated data processing transaction request fed back by one of more of the other blockchain nodes.

15. The blockchain-based data processing apparatus according to claim 13, wherein the instructions are executed by the at least one processor to enable the at least one processor to:
delete the updated data associated with the encapsulated data processing transaction request, or mark the updated data associated with the encapsulated data processing transaction request as data with an invalid state.

16. The blockchain-based data processing apparatus according to claim 13, wherein the instructions are executed by the at least one processor to enable the at least one processor to:
in response to determining that the local database includes other data with an unconfirmed state that depends on the invalid data, determine the other data with the unconfirmed state as invalid data, and determine another data processing transaction request associated with the other data with the unconfirmed state as an invalid request.

17. The blockchain-based data processing apparatus according to claim 13, wherein the instructions are executed by the at least one processor to enable the at least one processor to:
discard the encapsulated data processing transaction request, or generate an updated data processing transaction request according to the encapsulated data processing transaction request, and pre-executing the updated data processing transaction request.

18. The blockchain-based data processing apparatus according to claim 13, wherein the instructions are executed by the at least one processor to enable the at least one processor to:
perform response processing based on the data with the confirmed state and the data with the unconfirmed state in the local database, in response to receiving a data access request.

19. The blockchain-based data processing apparatus according to claim 13, wherein the instructions are executed by the at least one processor to enable the at least one processor to:
acquire a plurality of data processing transaction requests transmitted by the other blockchain nodes, and marking the plurality of data processing transaction requests as data processing transaction requests to be verified;
execute respective data processing transaction requests to be verified, and identify a conflict between the data processing transaction requests to be verified; and
refuse chaining, in response to identifying the conflicting data processing transaction request to be verified.

20. A non-transitory computer readable storage medium for storing computer instructions, implemented by circuits for implementing functions, wherein the computer instructions, when executed by a computer, cause the computer to:

acquire a locally generated data processing transaction request;

pre-execute the data processing transaction request, to determine a pre-execution result including write data;

update a data object in a local database according to the write data, and mark updated data of the data object as data with an unconfirmed state, before a consensus of other blockchain nodes is gained;

encapsulate the pre-execution result into the data processing transaction request, and transmit an encapsulated data processing transaction request to a blockchain network, to request other blockchain nodes to process the encapsulated data processing transaction request, wherein in the process of processing the data processing transaction request by other blockchain nodes, execute the data processing transaction request to acquire at least one execution result, wherein each of the at least one execution result is used to be verified if it is consistent with the pre-execution result; and determine updated data associated with the encapsulated data processing transaction request as invalid data, in response to determining that the blockchain network refuses to execute the encapsulated data processing transaction request; or mark the updated data associated with the encapsulated data processing transaction request as data with a confirmed state, in response to determining that the blockchain network executes the encapsulated data processing transaction request.

* * * * *